(12) United States Patent
Vanhanen et al.

(10) Patent No.: US 8,943,873 B2
(45) Date of Patent: Feb. 3, 2015

(54) METHOD AND DEVICE FOR DETECTING AEROSOL PARTICLES

(75) Inventors: Joonas Vanhanen, Helsinki (FI); Markku Kulmala, Helsinki (FI); Jyri Mikkilä, Helsinki (FI); Erkki Siivola, Riihimäki (FI); Mikko Sipilä, Helsinki (FI)

(73) Assignee: Airmodus Oy, Helsinki (FI)

( * ) Notice: Subject to any disclaimer, the term of this patent is extended or adjusted under 35 U.S.C. 154(b) by 315 days.

(21) Appl. No.: 13/261,060

(22) PCT Filed: Jun. 3, 2010

(86) PCT No.: PCT/FI2010/050455
§ 371 (c)(1),
(2), (4) Date: Feb. 17, 2012

(87) PCT Pub. No.: WO2010/139861
PCT Pub. Date: Dec. 9, 2010

(65) Prior Publication Data
US 2012/0131989 A1    May 31, 2012

(30) Foreign Application Priority Data
Jun. 5, 2009  (FI) .................................... 20090232

(51) Int. Cl.
*G01N 37/00*  (2006.01)
*G01N 1/38*  (2006.01)
*G01N 15/06*  (2006.01)

(52) U.S. Cl.
CPC ...................................... *G01N 15/06* (2013.01)
USPC ........................................... 73/28.01; 356/37

(58) Field of Classification Search
CPC ....................................................... G01N 15/06
USPC ................................................ 73/28.01; 356/37
See application file for complete search history.

(56) References Cited

U.S. PATENT DOCUMENTS 2,684,008 A * 7/1954 Vonnegut ........................ 356/37
5,072,626 A  12/1991 Ensor et al.
(Continued)

FOREIGN PATENT DOCUMENTS

CN           1163800 A        11/1997
KR    10-2005-0089897         9/2005
(Continued)

OTHER PUBLICATIONS

Sgro, Lee Anne, and Juan Fernandez de la Mora. "A simple turbulent mixing CNC for charged particle detection down to 1.2 nm." Aerosol Science and Technology 38.1 (2004): 1-11.*
(Continued)

*Primary Examiner* — Lisa Caputo
*Assistant Examiner* — Punam Roy
(74) *Attorney, Agent, or Firm* — Patterson Thuente Pedersen, P.A.

(57) ABSTRACT

Sizes or size distribution of aerosol particles of an aerosol gas stream is detected. A particle-free carrier flow is saturated in a saturator by a first condensing medium, after which, the carrier flow is mixed in a mixing section turbulently with aerosol particle flow. Advantageously, a plurality of separate mixtures with different saturation ratios are provided and introduced to the first condensing environment in order to condensate the condensing medium onto the aerosol particles. Depending on the saturation ratio, the particles with different lowest original size are activated and grown in a growing section and/or in the condensing environment. After activation and growing, the particles are detected by a detecting means.

19 Claims, 4 Drawing Sheets

(56) References Cited

U.S. PATENT DOCUMENTS

| | | | |
|---|---|---|---|
| 5,118,959 A * | 6/1992 | Caldow et al. | 250/573 |
| 5,903,338 A | 5/1999 | Mavliev et al. | |
| 6,194,028 B1 | 2/2001 | Horiuchi et al. | |
| 6,712,881 B2 * | 3/2004 | Hering et al. | 95/228 |
| 7,407,531 B2 * | 8/2008 | Flagan et al. | 95/154 |
| 7,975,564 B2 * | 7/2011 | Ulevicius et al. | 73/863 |
| 2004/0002166 A1 * | 1/2004 | Wiederin | 436/181 |
| 2004/0020362 A1 * | 2/2004 | Hering et al. | 95/228 |
| 2005/0248750 A1 * | 11/2005 | Flagan et al. | 356/37 |
| 2008/0152547 A1 | 6/2008 | Hopke et al. | |

FOREIGN PATENT DOCUMENTS

| | | |
|---|---|---|
| WO | WO 01/27589 A1 | 4/2001 |
| WO | WO 01/31312 A2 | 5/2001 |
| WO | WO 2005/066610 A1 | 7/2005 |

OTHER PUBLICATIONS

Vanhanen, J., et al. "Particle size magnifier for nano-CN detection." Aerosol Science and Technology 45.4 (2011): 533-542.*

P. Demokritou, T. Gupta, P. Koutrakis, "A High Volume Apparatus for Condensational Growth of Ultrafine Particles for Inhalation Toxicological Studies," Aerosol Science and technology 36:1061-1072 (2002).*

K. Okuyama, Y. Kousaka & T. Motouchi, "Condensational Growth of Ultrafine Aerosol Particles in a New Particle Size Magnifier", Aerosol Science and Technology, 3:4, 353-366 (1984).*

Z. Q. Zhang & B. Y. H. Liu, "Dependence of the Performance of TSI 3020 Condensation Nucleus Counter on Pressure, Flow Rate, and Temperature", Aerosol Science and Technology, 13:4, 493-504 (1990).*

Y. Kousaka, T. Niida, K. Okuyama, and H. Tanaka, "Development of a Mixing Type Condensation Nucleus Counter," J. Aerosol Sci. vol. 13, No. 3, pp. 231-240 (1982).*

R. Niessner, B. Daeumer & D. Klockow, "Investigation of Surface Properties of Ultrafine Particles by Application of a Multistep Condensation Nucleus Counter", Aerosol Science and Technology, 12:4, 953-963 (1990).*

Search Report for Chinese Patent Application No. 201080034558.1 dated Dec. 30, 2013, 2 pages.

* cited by examiner

600 Detection of aerosol particles

601 Introducing cleaned carrier gas flow to a saturator

602 Saturating the carrier gas flow

603 Heating the saturated carrier gas flow

604 Introducing sample comprising aerosol particles to a sample inlet

605 Cooling the flow comprising aerosol particles

606 Mixing the carrier gas flow and aerosol particle flow with each others to mixture

607 Introducing the mixture to a first condensation environment

608 Cooling the mixture in the first condensation environment

609 Condensing the condensing medium onto the aerosol particles

610 Introducing the mixture to a at least one further condensation environment for further condensation and growing

611 Detecting the growth aerosol particles

FIG. 6

700 Detection of aerosol particle size

601 → 602 → 603

604 → 605

701 Adjusting the flow rate of the carrier flow

606 → 607 → 608 → 609 → 610 → 611

702 All saturation ratios monitored — NO (loops back to 701)

YES ↓

703 Providing information about sizes or size distribution

FIG. 7

METHOD AND DEVICE FOR DETECTING AEROSOL PARTICLES

PRIORITY CLAIM

The present application is a National Phase entry of PCT Application No. PCT/FI2010/050455, filed Jun. 3, 2010, which claims priority from Finnish Application Number 20090232, filed Jun. 5, 2009, the disclosures of which are hereby incorporated by reference herein in their entirety.

TECHNICAL FIELD OF THE INVENTION

The invention relates to generally to detection of aerosol nanoparticles, and more particularly, to detection of aerosol particles having different sizes. Specifically, the invention relates to detection of aerosol particles having sizes smaller than optically detectable sizes in addition to detecting the size or size distribution of the aerosol particles.

BACKGROUND OF THE INVENTION

Aerosol particles occur in the air we inhale and may have an adverse effect on the human health. In addition, inhalers produce different kinds of aerosol particles of different sizes, including nanoparticles where not only the presence but also the size distribution of the aerosol particles is an object of the interest. Furthermore, the detection of the aerosol particles and characteristics, such as their generation and the size, is essential in climate study and monitoring exhaust gasses and implementation of emission standards.

One barrier to the detection of aerosol particles having a diameter of less than the wave length of light is that they cannot be detected optically. A number of techniques exists for detecting aerosol particles having a size smaller than optically detectable, such as first charging the aerosol particle. The charged particles are collected and the induced electric current is measured in order to detect the presence or amount of the particles. Also, some detection techniques involve growing the aerosol particles by condensing a certain condensing fluid vapour on the aerosol particles before attempting detection.

The known methods have a number of drawbacks. Specifically, charging the particles before detecting makes the detecting device more complicated. Also, the charging may change the structure of the particles, such as the size of the particles and even decompose them (especially the smallest ones). In addition, the charging may produce particles whose size may match the size of the particles to be detected and thereby disturbing the actual measurement. In the charging method, the charging probability must also be known for particles of different sizes in order to detect the total numbers of particles. The charging probability is, however, very difficult to determine for the smallest particles.

In addition, the size or size distribution of the nanoscale aerosol particles cannot be detected but the known method relates mainly to particle counting or to indicating the presence of the aerosol particles.

SUMMARY OF THE INVENTION

The present invention is concerned with a detection of aerosol particles by growing them before detection by a condensation.

According to an embodiment of the invention, aerosol particles of an aerosol gas stream are grown before detecting. The growing can be implemented by condensing a condensing medium onto the aerosol particles. According to an embodiment, a particle-free carrier flow, such as filtered air, is first saturated in a saturator with the condensing medium-afterwhich the saturated particle-free carrier flow is mixed with an aerosol gas stream comprising said aerosol particles to be grown and detected. The carrier flow carries both the aerosol particles to be grown and detected as well as also the first condensing medium.

According to an embodiment, aerosol nanoparticles can be mixed in a turbulent and adiabatic process to minimize or prevent any transfer heat with the environment to accurately determine the saturation ratios. In addition, the flow rate of the aerosol gas stream is kept relatively fast in order to prevent the loss of the aerosol nanoparticles to be detected through diffusion of the nanoparticles on the walls or other structures of the device or detecting arrangement.

After mixing the saturated particle-free carrier flow and the aerosol gas stream of aerosol nanoparticles, the mixture is introduced to a condensation environment (e.g. a condensation chamber). The condensation environment is adapted to cause the condensing medium, which comprises the saturated particle-free carrier flow, to condensate on the aerosol particles of the mixture. According to an embodiment, the condensation (or activation) can begin before the saturated carrier flow reaches the condensation environment when the aerosol particles are mixed with the saturated carrier flow-as a result of different temperatures of the flows.

According to an embodiment, the condensation in the condensation environment can be implemented by keeping the condensation environment temperature lower than the temperature of the saturated particle-free carrier flow and heating said saturated particle-free carrier flow to a temperature warmer than the aerosol particle stream. The temperature of the condensation medium governs the temperature of the condensation environment.

According to an embodiment, the aerosol particle stream can comprise a lower temperature than the saturated particle flow. The aerosol particle stream can have a temperature between 5 to 20 C according to an embodiment, or about 8 C according to another embodiment. The saturated particle free carrier flow can have a temperature between 70 to 80 C according to an embodiment, or about 77.5 C according to an embodiment. Similarly, the condensing environment can comprise a lower temperature than the aerosol particle stream in order to enhance the cooling after the mixing and thus amplify the growth of the activated aerosol particles by condensation. The condensing environment can have a temperature between −2 to +5 C according to an embodiment and about 0 C according to another embodiment. After growing the aerosol particles the droplets can be detected and counted by an external particle counters using optical counting, filtering and weighing the filtered particles, and/or ionizing and measuring the electric current.

According to an embodiment, the saturation ratio of the mixture can be changed to provide a plurality of separate mixtures of the saturated particle-free carrier flow and aerosol particles having different saturation ratios. The mixtures with the different saturation ratios are then introduced separately to the condensation environment in order to determine the sizes or size distribution of the aerosol nanoparticles. The saturation ratio determines probability of the lowest aerosol particle size to be grown, wherein the higher the saturation ratio the smaller the initial size of the aerosol particles which the condensing medium is condensed on and which are grown to the detectable size. When the correlation between the different saturation ratios and the lowest sizes are known, the sizes or size distribution of the particles detected can be determined based on the used saturation ratios.

According to an embodiment, the different saturation ratios can be achieved by changing the mixing ratio of the saturated particle-free carrier flow and the aerosol gas stream, and/or by altering the temperature difference between the saturated particle-free carrier flow and the aerosol gas stream. Since the mixing ratio is determined by the flows through the saturator (saturated particle-free carrier flow) and the total flow after the mixing (the combined carrier flow and the particle flow), the mixing ratio and thereby the saturation ratio can be varied by changing the flow rate of the saturated particle-free carrier flow and/or the aerosol gas stream. According to an embodiment, the flow rate of the saturated particle-free carrier flow can be changed while keeping the aerosol gas stream flow as constant as possible. The constant aerosol gas stream flow allows for a known amount of the possible aerosol particle diffusion losses and can be taken into account much easier.

According to an embodiment, at least two separate mixtures of said saturated particle-free carrier flow and aerosol particles having different saturation ratios are introduced separately to a condensing environment in order to condense the condensing medium onto the aerosol particles of the mixtures. Depending on the saturation ratio of the mixture, the aerosol particles with a certain lowest initial size and particles having size bigger than this lowest initial size are activated, grown and detected with certain probabilities. When the correlation between the used saturation ratios and the lowest size of the particles to be condensed with each saturation ratio is known, a size spectrometer capable of detecting aerosol particles with different lowest initial sizes can be provided by changing and scanning the mixing or saturation ratios. This embodiment provides an effective and accurate tool to probe the number size distribution at sizes starting from about 1 to 5 nm according to an embodiment and 1 nm according to another embodiment which is where the gas-to-particle conversion occurs.

According to an embodiment, the mixtures are to at least one second condensing environment comprising a second condensing medium in order to condense said second condensing medium on the aerosol particles of the mixtures to further grow said aerosol particles before detecting. According to an embodiment, the initial aerosol particle size may be between 1-5 nm. According to an embodiment, the particle sizes can be about 100 nm after the first condensation environment and 1 µm after the second condensation environment, which are already optically detectable sizes. The sizes of the particles presented here are only examples and the final size depends on the used condensing medium, flow rates and temperatures and any other parameters affecting to the saturation ratio, as well as also of the initial size of the particles and of the structural, physical and/or chemical compositions and features of the particles.

The lower limit in the diameter of the particle that can be detected is determined by the properties of the condensing vapour. Some vapours can activate very small particles to grow, but cannot grow the particles enough up to optically detectable sizes due to low vapour pressure. The activation means the "potential barrier" in the condensation after which the particle size starts to grow due to condensation. Similarly, other condensing vapours cannot activate the smallest particles, but they can grow the already activated particles very quickly. According to an embodiment of the present invention comprises separately using two different condensing vapours to activate and grow also the smallest aerosol particles up to optically detectable sizes, wherein the first condensing medium typically activates and minimally grows the particles and after which the second condensing medium grows the activated particles more effectively.

According to an embodiment of the present invention, the first condensing medium is a vapour having optimal properties to activate and condense on the smallest particles such as those ~1 nm and larger, and the second condensing medium is a fluid having optimal properties to further grow particles quickly to optically detectable sizes. According to an embodiment, the second condensing medium is adapted to grow the particles to optically detectable sizes in a few seconds. According to an embodiment, the first condensing medium has low saturation vapour pressure and high surface tension providing high saturation ratios, but still preventing the homogeneous nucleation. The higher the surface tension of the condensation vapour droplets, the smaller condensation vapour droplets can be achieved without the homogeneous nucleation. In addition, according to an embodiment the second condensing medium has high saturation vapour pressure and high diffusivity in the air so that the second condensation environment is continuously maximally saturated by said second condensing fluid thus enabling continuously, fast growth of the particles to optically detectable sizes.

According to an embodiment, the used condensing medium can be diethylene glycol, oleic acid, propanol, butanol, glycerol and/or water. According to an embodiment, the first and the second or any further condensation environments use different condensing mediums. According to another embodiment, at least two of the condensation environments, such as the first and the second condensation environments use the same condensing medium. According to an embodiment, the first condensing medium is diethylene glycol and the second or other further condensing medium is water, which can grow aerosol particles to optically detectable sizes.

According to an embodiment, the flow rate of the aerosol gas stream is maintained at a constant and relatively high rate in relation to the dimensions of the conduits or flow channels or saturated particle-free carrier flow in order to keep diffusion losses of the aerosol particles minimal. The flow rate of the aerosol gas stream 2-5 l/min in a flow conduit having a 4mm inner diameter according to an embodiment and about 2.5 l/min in a flow conduit having a 4 mm inner diameter according to another embodiment. The saturated particle-free carrier flow rate can be varied to change the saturation ratios of the mixture to select the initial aerosol particle size to be grown and detected. The saturated particle-free carrier flow rate is varied between 0.05 and 5 l/min according to an embodiment or between 0.3 and 1.0 l/min according to another embodiment. According to an embodiment, the flow rate can be changed in the same relation to the dimensions of the flow conduits such as the diameter of the conduits.

According to an embodiment, the separate mixtures can be provided and introduced to the condensation environment(s) either at the same time, such as using different introducing channels or flow conduits for each separate mixtures, or separate mixtures with different saturation ratios in sequences separated by certain time intervals for example, during which the flow rate and thus saturation ratios are changed such that the structure of the detecting arrangement can be much simpler.

According to an embodiment, the sample aerosol particles can be in solid phase, or that the sample aerosol particles can be in liquid phase. According to an embodiment, the sample aerosol particles can be partly in the liquid phase and partly in the solid phase; such as a particle having solid core and liquid surface.

Unlike electrical detection, the present invention enables counting of particles and detecting their sizes without the need of charging the particles at all so the electrically neutral particles can also be detected. Moreover the condensation techniques of the invention with different saturation ratios allows for selection of the initial lower size of the particles to be grown very accurately thereby providing an accurate size spectrometer for detecting the sizes and size distributions of aerosol and airborne particles and molecular clusters down to ~1nm according to an embodiment. According to an embodiment, the size spectrometer can be provided e.g. by scanning only the mixing ratio. The device of the invention can be able to detect even single particles.

In addition, the using of plurality of sequential condensations has the advantage of can more effectively grow the particle to the desired or detectable size. The first condensing medium can be selected to activate the particles to grow and—with additional condensing medium(s) selected to grow the already activated and possibly slightly grown particles to the desired or detectable size, allowing greater enlargement of the nanoparticles than would be achieved with a single condensing fluid and thereby also providing the advantage of increased detection sensitivity.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which:

FIG. 6 is an exemplary method for growing and detecting the aerosol particles according to an advantageous embodiment of the invention, and FIG. 7 is an exemplary method for detecting sizes or size distribution of aerosol particles according to an advantageous embodiment of the invention.

Figure 1:
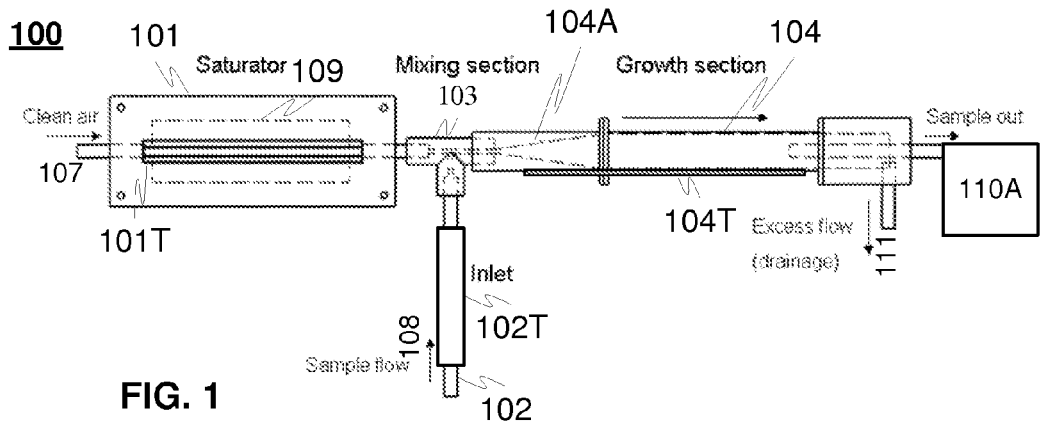
FIG. 1 is an exemplary arrangement for growing and detecting the aerosol particles according to an advantageous embodiment of the invention, FIGS. 2A,B is a exemplary arrangement for growing and detecting the aerosol particles with plurality of condensation chambers according to an advantageous embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

FIG. 1 illustrates arrangement or device 100 for growing and detecting aerosol particles, according to an embodiment of the invention, wherein the arrangement 100 comprises a saturator 101 for saturating a particle-free flow 107 with a condensing medium, a sample inlet 102 for providing aerosol stream 108 comprising aerosol particles into the detection arrangement 100, and a condensation chamber 104, where the condensing medium is adapted to condense onto the aerosol particles 108. The particle-free flow 107 is, according to an embodiment, filtrated clean air introduced to the saturator via a clean air inlet.

The saturator 101 comprises, according to an embodiment, a sintered tubing 109, such as sintered stainless steel tubing, surrounded by the condensing medium, such as diethylene glycol (DEG) inside a casing. The casing is advantageously made of metal, such as aluminium, but can also be any other suitable material, such as composite material. The porosity of the sintered tubing is chosen so that surface tension of condensing medium prevents it from flowing through the pores as a liquid. According to an embodiment, the saturation ratio of the condensing medium is near unity at the inner wall of the tubing. By using the sintered tubing, the filling of the saturator 101 can be done passively by using only hydrostatic pressure of the condensing medium rather than liquid pumps.

According to an embodiment, the saturator 101, the sample inlet 102, and/or the condensation chamber 104 are also provided with temperature control means for controlling the flow temperatures to provide optimal environments having desired saturation ratios and condensation environment in the condensation chamber 104. According to an embodiment, the saturator 101 can comprise temperature controller 101T for controlling the temperature of the particle-free carrier flow 107. According to an embodiment, the particle-free carrier flow can be heated by the temperature controller 101T for example to 77.5° C. before mixing. By heating the particle-free carrier flow, more of the condensing medium used by saturating said carrier flow can be placed into the vapor phase to enable a greater degree of droplet growth.

According to an embodiment, the inlet means 102 can also comprise a temperature controller 102T adapted to control the temperature of the aerosol particle flow 108. According to an embodiment, the temperature of the aerosol particles flow 108 is cooled down to 18° by the temperature controller 102T before mixing.

The arrangement 100 also comprises a mixing section 103 structurally and functionally connecting the saturator 101, sample inlet 102 and the condensation chamber 104 with each other. The mixing section 103 is adapted to turbulently and adiabatic mix the saturated particle-free carrier flow and flow of aerosol particles. According to an embodiment, the mixing section 103 is constructed from plastic or other low heat conducting materials in order to avoid heat transfer between the heated saturator and the cooled aerosol inlet and thereby providing a more constant and accurate saturation ratio, which can be determined by monitoring the flow rate of the carrier flow. It should be noted that the plastic can be an anti-static plastic to prevent losses of ions in the case where the flows comprise ions. The connections can be implemented by pathways, such as pipes or tubes. According to an embodiment, the inner diameter of the mixing section is about 1.7 mm. The diameters and lengths of the flow channels can be varied to adjust the flow rates.

Inside the mixing section 103, the saturation ratio of the first condensing medium is adapted to increase rapidly and the fluid may also start to condense onto the surface of the sample aerosol particles to activate the particle for growth. The mixture is led from the mixing section 103 to the first condensation environment 104 such as the first condensation chamber 104. According to an embodiment, the arrangement can also comprise a special growth section 104A before the actual condensation chamber 104 into which the flow is introduced after mixing to the condensation chamber 104 via the growth section 104A.

The condensation environment 104 (either chamber, growth section or both) comprises a temperature controller 104T for controlling the temperature of the condensation environment and thereby the temperatures of the mixture entering into and travelling through the chamber 104. According to an embodiment, the mixture is cooled by the temperature controller 104T to 0° C. in order to enhance the condensation of the condensing medium onto the particle surfaces to amplify the growth of the activated aerosol particles to be detected.

According to an embodiment the growth section 104A can comprise conical tubing. According to an embodiment, the diameter of the first 5 cm of said conical tubing changes from 1.7 to 16 mm. The broader end of the conical tubing is integrated or transitions into the condensation chamber, which can comprise 10 cm stainless steel tubing having a 16 mm inner diameter according to an embodiment. The dimensions discussed here are only examples of an embodiment and that they can be varied, as understand by the skilled person. According to an embodiment there is no conical portion, but only a tube or tubes.

After the condensation chamber 104, the mixture can either be led to particle detection means 110A, 110B, such as particle counter such as a CPC Condensation Particle Counter, 110A if the particle size is below the optically detectable size and OPC Optical Particle Counter, 110B if the particle size is optically detectable. According to an embodiment, the mixture can be led to a second or additional condensation chamber 105, 125b for further growth of the sample aerosol particles to optically detectable sizes, as is described in FIGS. 2A, B.

According to an embodiment, the second condensation chamber 105 comprises tubing, such as sintered stainless steel tubing 106 surrounded by the condensing medium as with the tubing in connection with the saturator 101 or wetted by a second condensing medium, such as water. The second (or any additional) condensing environment can also comprise a temperature controller 105T, 125T for controlling the temperature of the second (or any further) condensing environment, either to heating or cooling.

The properties, such as temperatures, of the second or any other additional condensing environment 105,125b depends on the properties of the condensing medium used in said second or any other additional condensing environment, such as the diffusivity of the condensing medium. According to an embodiment, if the condensing medium is a medium having higher diffusivity in air than heat, such as water or methanol, the temperature of the next condensing environment 105 (already saturated by said condensing medium, such as water) is higher than the temperature of the flow before said condensing environment so that the particles will grow fast and effectively.

According to an embodiment, if the condensing medium is a medium having lower diffusivity in air than heat, such as n-butanol, the temperature of the next condensing environment 105, 125b, wherein the flow inside the condensing environment is already saturated by said condensing medium, is lower than the temperature of the flow before said condensing environment.

Figure 2A:
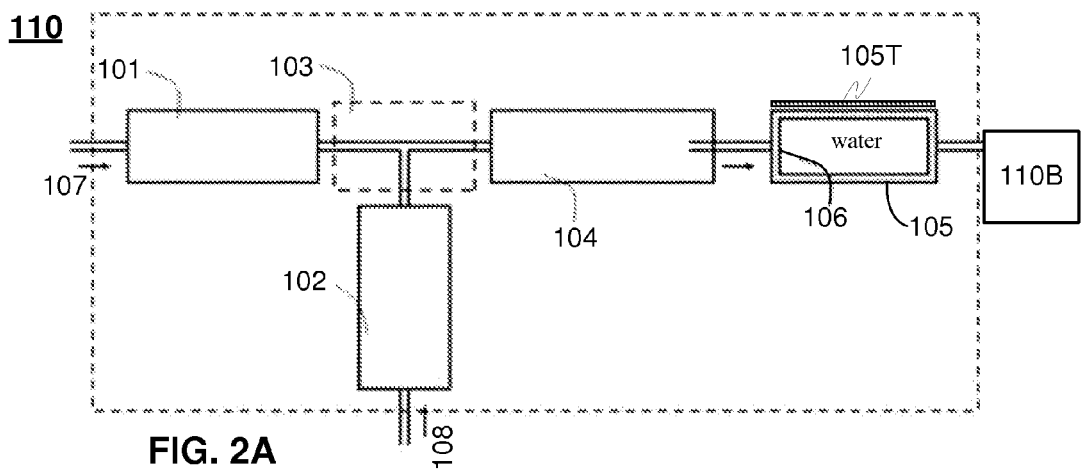
Figure 2B:
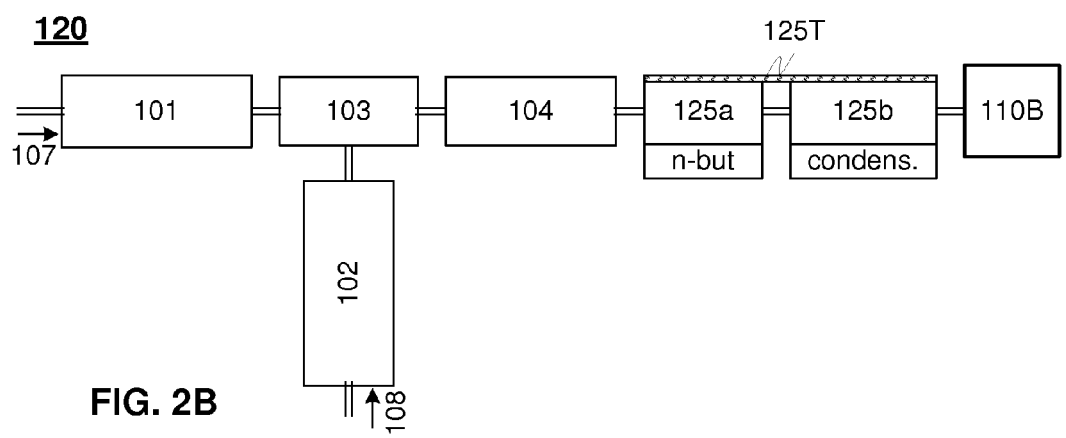

According to an embodiment, the flow can be saturated by the condensing medium before introducing said flow into the condensing environment, such as is depicted in FIG. 2B. The chamber 125a is a saturator comprising the second (or additional) condensing medium by which the flow flowing through the saturator is advantageously saturated. Said second (or additional) condensing medium can be butanol, wherein the saturation environment 125a comprises a much higher temperature than the flow before said saturation environment 125a. In this embodiment the condensation environment 125b and correspondingly the flow inside the condensation environment 125b after said saturator 125a has the temperature lower than the temperature of said saturation environment 125a in order to provide effective condensation of the second (or additional) condensing medium onto the particles in the condensation chamber 125b.

According to an embodiment, when the second or further condensing medium is water or other medium having higher diffusivity in air than heat the mixture in the second condensing environment is heated by the temperature controlling means 105T to higher temperature than the temperature of the mixture leaving the previous condensation environment 104. This creates a high saturation ratio for the additional condensing medium, wherein the condensing medium starts to condense rapidly onto the aerosol particles growing them to optically detectable sizes, including to size of 1 μm. After this the particles can be counted by optical detecting counting means 110B.

According to an embodiment, the growth particles are led from the last condensing environment (104, 105, 125b or from any additional environment) to the counter 110A, 110B via 6 mm tubing, but again the diameter or other dimensions of the tubing can vary as previously discussed. The counter 110A, 110B can be CPC if the particles are not grown to the optically detectable sizes or some other type of direct particle detector or any other counter capable of detecting the growth particles. The detection means can comprises memory means for storing the detection results and environmental conditions, such as temperatures and flow rates of the flow in different portions of the arrangement, as well as the saturation and/or mixing ratios. In addition, the arrangement can comprise an adjusting means for adjusting the flow rates, such as the flow rate of the carrier flow, to change the saturation ratio to the desired one in order to detect particles with a certain size.

According to an embodiment, the flow through the saturator 101 and possible excess flow 111 are controlled with flow controlling means, such as needle-valves and/or voltage or current adjustable pumps. According to an embodiment, the difference of the flow through the saturator 101 and the excess flow determines the inlet flow rate 102. The inlet flow rate is kept constant, such as for at 2.5 l/min according to an embodiment, and the saturator flow rate is varied between 0.05 and 5 l/min according to an embodiment and most between 0.3 and 1.0 l/min according to another embodiment. According to an embodiment, the flow rates are measured by pressure difference gauges. Temperatures can be measured from the surfaces of the saturators 101, 125a, the inlet 102 and the condensing environment 104, 105, 125b or possible growth section 104A. According to an embodiment, the temperatures can be measured from the flow through the inlet 102 with thermistors or other suitable means know by the skilled person. The temperature of the saturators 101, 125a, as well as the condensing chambers 104, 105, 125b can be controlled by using heating-resistors connected to a proportional-integral-derivative (PID) controller (not shown in the Figures).

According to an embodiment, the Pecklét number (Pe), which describes the heat conductivity, is between 1500 and 1000 at the above mentioned flows, and the Reynolds number (Re) describing the turbulence between 5000 and 3000. As the flow inside the 15 T-part of the mixing section 103 is turbulent, the conduction of heat can be neglected. Generally, increasing turbulence and preventing heat conduction increase the saturation ratio achieved inside the mixing section 103. It is to be also noted that the invention is not however limited to the values above, but any other appropriate values can be applied.

Figure 3:
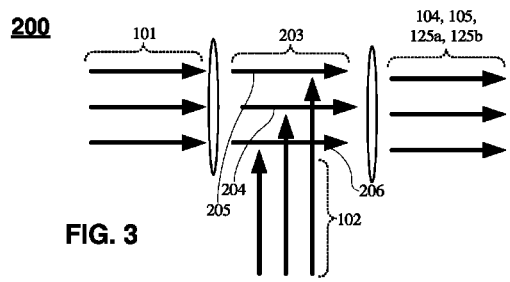
FIG. 3 is an exemplary aerosol particle size spectrometer arrangement for growing and detecting the aerosol particles size distribution according to an advantageous embodiment of the invention.

FIG. 3 illustrates an arrangement 200 and mixing section 203 of an aerosol particle size spectrometer for growing and detecting the aerosol particles size distribution according to an embodiment of the invention, wherein the separate mixtures with different saturation ratios are provided simultaneously. The arrangement 200 comprises a plurality of conduits 204, 205, 206. The conduits can be selected so that they adapt the flow rate of the saturated particle-free carrier flow from the saturator 101 and/or the flow rate of the aerosol particle flow from the sample inlet 102 to provide a plurality of different mixture flows each having its own saturation ratio. According to an embodiment, the pressure of the carrier flow after the saturator can be the same, but the flow difference and thereby the different saturation ratios can be achieved by conduits having different diameters and thus providing different flow rates. According to another embodiment, the pressures and thereby the flow rates of the flows of each conduits can be different thereby providing number of different saturation ratios. As previously discussed, the saturation ratio determines the lowest particle size to be grown at a certain probability.

According to an embodiment, the conduits or mixing section 103 of the arrangements described in FIGS. 1 and 2A, B can be replaced by the mixing section 203 or number of conduits 204, 205, 206 described in FIG. 3. According to an embodiment, the mixing section 203 or plurality of conduits 204, 205, 206, the saturating and/or condensing environments can also be adapted to manage the plurality of separate mixture flows. This can be implemented by providing the saturating and/or condensing environments with a plurality of separate conduits (not shown in Figures).

Thus the arrangement and/or the mixing section 203 with conduits 204, 205, 206 provide a plurality of mixtures with different saturation ratios thereby providing a size spectrometer for detecting the size distribution of the aerosol particles. By using the arrangement 200 and/or the mixing section 203 with the number of conduits, the plurality of separate mixture can be detected at the same time. According to an embodiment, the mixing section 103, as depicted in FIGS. 1 and 2A, B, can be used to achieve the separate mixtures by detecting the first flow at the first time interval, then changing the saturation ratio and detecting the second flow at the second sequential time interval, and repeating the steps as many times as necessary.

Figure 4:
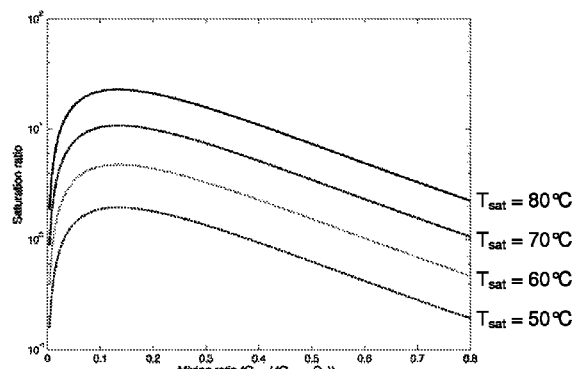
FIG. 4 is an exemplary saturation ratio inside the arrangement as a function of mixing ratio with different saturator temperatures according to an advantageous embodiment of the invention, where the temperature of the aerosol sample is kept at 16° C.

FIG. 4 illustrates an saturation ratio as a function of mixing ratio with different saturator temperatures, according to an embodiment of the invention, wherein the temperature of the aerosol sample comprising aerosol particles to be detected is kept at 16° C. The basic principle of a particle size magnifying device (PSM) is to produce high saturation ratio by turbulently mixing heated clean air saturated by the condensing medium with an aerosol sample having a lower temperature than the saturated air. This creates a high saturation ratio for the working fluid. The saturation ratio is defined by the ratio of actual vapour pressure and the equilibrium vapour pressure at temperature T.

$$S(T) = \frac{p_v}{p_{eq}(T)} \tag{1}$$

If the mixing of the sample flow with the saturated carrier flow is assumed to be rapid and adiabatic, the temperature and the vapour content after mixing can be defined as:

$$T_i = (C_{sat}T_{sat}Q_{sat} + C_aT_aQ_a)/C_{mix}Q_{tot} \tag{2}$$

$$H_i = Q_{sat}H_{sat}/Q_T, \; Q_T = Q_{sat} + Q_a \tag{3}$$

where C is the specific heat, Q is the flow rate and H is the vapour content of the air.

$$H = \frac{M_{DEG}}{M_{AIR}} \frac{p_v}{p_{ATM} - p_v}, \tag{4}$$

where $M_{DEG}$ and $M_{AIR}$ are the molecular masses of diethylene glycol (used as condensing medium) and air (used as carrier flow), $p_v$ is the vapour pressure and $p_{ATM}$ is the atmospheric pressure.

In FIG. 4, the saturation ratio calculated according to the equations 1-3 is presented as a function of mixing ratio for four different temperatures of the saturator. The mixing ratio is defined as the ratio between the flows through the saturator and the total flow after the mixing. After the saturator, the air stream is fully saturated. According to an embodiment, temperature of the aerosol sample was kept at 16° C. The saturation ratio increases steeply as the mixing ratio increases and to a theoretical maximum at around mixing ratio of 0.15, after which it starts to decrease. Also, at higher temperatures, the saturation ratio is generally elevated. The saturation ratio of the condensing medium in the PSM can be adjusted both by adjusting the mixing ratio and by altering the temperature difference between the saturated flow and the sample flow.

The activation and growth of an aerosol particle are mainly dependent on the size of the particle. The smaller the particle, the higher the saturation ratio needed for activation. Also, chemical composition and charge can have an effect, especially for the small particles (<3 nm in diameter). If only size is taken into account, the critical diameter in a certain saturation ratio S is defined by a Kelvin equation:

$$d_c = \frac{4\sigma M}{RT\rho \ln(S)}, \tag{5}$$

where σ is the surface tension of the solution, M is the molecular mass of the condensing vapour, R is the universal gas constant, T is temperature and ρ is the density of the solution. For small particles, the heterogeneous nucleation probability has to be taken into account as well as also possible charging of the particles.

In order to achieve high enough saturation ratios to activate and grow nanosized particles without homogeneous nucleation, a proper condensing medium has to be used. When using condensing medium of low vapour pressure and high surface tension, high saturation ratios can be achieved without homogeneous nucleation. According to embodiment, diethylene glycol is used as the condensing medium for activating nanosized particles. According to an embodiment, other mediums can be including, but not limited to oleic acid.

Figure 5:
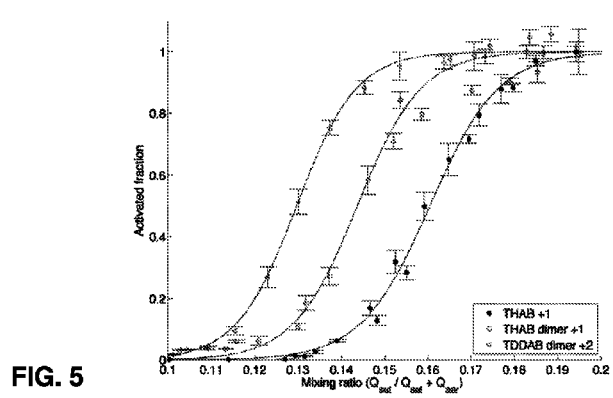
FIG. 5 is an representative example of an activated fraction of the particles as a function of the mixing ratio (Qsat/(Qsat+Qaer)) for aerosol particles having different initial sizes according to an advantageous embodiment of the invention, (TMAI monomer, THAB monomer, THAB dimer and TDDAB +2 dimer 5 with mobility diameters of 1.05, 1.47, 1.78 and 2.51 nm, respectively)

FIG. 5 illustrates an embodiment of the present invention in which an activated fraction of the particles as a function of the mixing ratio (Qsat/(Qsat+Qaer) and thus also as a function of saturation ratio) for aerosol particles having different initial sizes. The activated fraction is normalized in FIG. 5 to unity (1) and illustrates the probability that the aerosol particles having different initial sizes will be condensed and thus growth with a certain mixing or saturation ratio. The used particles and their sizes and charges are as:

THAB monomer 1.47 nm (+1)
THAB dimer 1.78 nm (+1)
TDDAB dimer 2.51 nm (+2)

The activated fraction (or nano condensation nucleus) is calculated by assuming that the sampling efficiency depicts the maximum possible counting efficiency (unity) such as normalizing the detection efficiency to the penetration efficiency of the PSM. The onset mixing ratio is defined as the mixing ratio where the activated fraction is 50%. The onset mixing ratio increases with decreasing mobility diameter when comparing TDDAB dimer, THAB dimer and THAB monomer.

As the saturation ratio (or mixing ratio) determines the initial lowest sizes of the particles to be activated and growth accurately, the arrangement of the invention provides a plurality of separate mixtures with different saturation ratios can be used as a size spectrometer for the smallest aerosol particles as the mixing ratio is scanned and subsequently the particles of different size are detected with the detection means. This provides a nice tool to investigate aerosol particle number size distribution for example below 3 nm size range. According to an embodiment, the size determined by measuring onset of heterogeneous nucleation doesn't easily convert to a mobility equivalent diameter achieved from e.g. DMA classification.

As can be seen in FIG. 5, the smaller the mixing ratio the larger the initial size of the particles to be activated and growth and vice versa, the higher the mixing ratio the smaller the initial size of the particles to be activated. According to an embodiment, a mixing ratio of about 0.12 essentially only TDDAB dimer +2 particles are activated and grown, but not the smaller ones, such as THAB dimer +1 or THAB +1 particles. When the mixing ratio is increased to about 0.14, a portion of THAB dimer +1 particles are activated and grown in addition to larger particles, such as said TDDAB dimer +2 particles. Similarly, when the mixing ration is increased to about 0.16, a portion of THAB +1 particles are also activated and growth. The larger particles are also activated and grown, wherein the sizes or size distribution of the larger particles can be determined by subtracting the amount of the particles detected by using the different mixing/saturation ratios.

FIG. 6 illustrates an exemplary method 600 for growing and detecting the aerosol particles according to an advantageous embodiment of the invention, where a carrier gas flow which does not comprise any particles, is introduced to the saturator at step 601, where the carrier flow is fully or at least partly saturated by a condensing medium at step 602. The carrier gas flow may also be cleaned before saturating at step 601. The temperature of the carrier gas may also be set, such as heated, to a desired level at step 603.

At step 604 a sample flow comprising aerosol particles to be detected is introduced into a sample inlet and the temperature of the sample flow is set, such as cooled, to a desired level at step 605. It should be noted that the steps 601-603 and 604-605 are typically applied at the same time but in different inlets or chambers of the arrangement. However, after managing the carrier gas flow and the flow comprising the aerosol particles they are mixed in the mixing section at step 606 in order to provide a mixture. The mixture is thus defined as the combination of saturated particle-free carrier gas and aerosol particles.

After mixing the mixture is introduced to a condensation environment at step 607. In an embodiment, the mixture is cooled (or warmed, depending on the used condensing medium as discussed elsewhere in this document) in the condensation environment at step 608 to a lower temperature than it was after the mixing. In the condensation environment the condensing medium used for saturating said carrier flow advantageously condensates on the aerosol particles in the mixture at step 609 and activates and grows the particles. After condensation environment the mixture comprising the already active and grown aerosol particles is introduced to a particle detecting means at step 611.

It should be noted that the method 600 may also comprise further condensations, where additionally some further condensing mediums are condensed on the aerosol particles for example at step 610, so after the first activation and growth of the aerosol particles. In the further condensations at step 610 the mixture may be additionally handled, such as saturated, reheated and/or cooled and different kind of condensing mediums can be used for further growing said particles, as is described elsewhere in this document. The step 610 is however optional.

After managing the carrier gas flow and the flow comprising the aerosol particles, the mixing ratio and also the saturation ratio is adjusted to a predetermined level at step 701 in order to activate and grow (and thus also detect) particles with a certain lowest initial size (as well as also the particles having diameter larger than the lowest initial size). The adjusting or changing of the saturation ratio can be implemented as described elsewhere in this document, such as changing the flow rate of the particle-free carrier gas flow.

After growing and detecting the aerosol particles, the process can be continued (step 702). If all desired saturation ratios are not yet monitored, the saturation ratio can be changed again in step 701 and the steps 701, 606-611 and 702 can be repeated as many time as necessary, so as long as all the desired saturation ratios and corresponding particle detections are monitored. The process is stopped at step 703, whereupon the final result can be displayed, such as counted particles of each used saturation ratios. The sizes or size distributions can be achieved by subtracting the amount of the particles detected by using the different mixing/saturation ratios from each other, since a certain saturation ratio will activate and grow particles having initial size at least or over a lowest threshold size. The lowest size of the particles to be activated and growth depends on the used saturation ratio.

According to an embodiment, a first used saturation ratio will activate and grow the particles having size of 5 nm and over, while the second used saturation ratio will activate and grow the particles having size of 4 nm and over. The numbers of particles having size of 4 nm can be determined by subtracting the amount of the particles detected by said first saturation ratio from the amount of the particles detected by said second saturation ratio.

According to an embodiment, the invention relates to a computer program product having computer readable code means, which are adapted to perform the steps of methods 600 and 700, when said computer program product is run on the computer. According to an embodiment, the computer program product is adapted to perform the steps such as opening and/or closing the valves; adjusting the voltage or electric current of the pumps; other flow controlling means of the arrangement such that the flow rates of the different flows are adjusted as desired measuring and analysing temperatures of the flows and either control the temperature controlling means to heat or cool down the flows to a certain desired temperature for example in order to achieve a certain desired saturation ratio. According to an embodiment, the computer program product can also comprise means for analysing the output signals of the detecting means in order to determine for example particles size or size distribution of the aerosol particle flow as described elsewhere in this document, when the relation between the saturation ratio and the lowest size of the particles to be activated and growth by said saturation ratio are known.

In addition the invention relates to a device having the all components of the arrangement 100, 110, 120 or 200 described above. The device can be a mobile device or even handheld device comprising a control logic for controlling the functioning of the components of the device as well as also means for calculating and displaying the results. The control logic can be implemented by hardware and/or software.

In the previous methods the first condensing medium is chosen so that it can be used to grow small aerosol particles by condensation, such as particles of sizes between 1-5 nm. This may prevent it from growing particles fast enough and why a second condensation environment may be needed to reach the optically detectable sizes. The second condensing medium is chosen such that it is soluble with the first condensing medium and can grow particles rapidly, typically in few microseconds. According to an embodiment, diethylene glycol is used as the first condensing medium and water as the second condensing medium.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. Especially the described embodiments can be combined with other embodiments, such as saturation ratios can be changed in the arrangement comprising either one or plurality of condensing environments and the temperatures of the second or further condensing environments of different embodiment may vary or be different in relation other embodiment or embodiments described above depending for example on the used condensing medium, as discussed above in this document.

The invention claimed is:

1. A method for detecting different size or size distribution of aerosol particles of an aerosol gas stream, the method comprising the steps of:
saturating particle-free carrier flow by a first condensing medium to provide saturated particle-free carrier flow;
mixing said saturated particle-free carrier flow with said aerosol gas stream comprising said aerosol particles, and preventing loss of ions by performing said mixing in a mixing section made of anti-static plastic;
providing at least two separate mixtures of said saturated particle-free carrier flow and aerosol particles, said mixtures having different saturation ratios;
introducing said mixtures separately to a first condensing environment in order to condense said first condensing medium onto the aerosol particles of the mixtures so that the mixture having the first saturation ratio is condensed onto the particles having different initial size than the mixture having the second different saturation ratio, wherein said condensation causes the aerosol particles to grow; and
detecting said growth of aerosol particles of different mixtures separately after said condensation;
wherein the original lowest particle size of the particle detected is determined by the used saturation ratio so that the higher the saturation ratio the smaller the lowest original particle size.

2. The method according to claim 1, wherein the different saturation ratios are achieved by changing the flow rate of the saturated particle-free carrier flow and/or the aerosol gas stream, and/or by altering the temperature difference between the saturated particle-free carrier flow and the aerosol gas stream.

3. The method according to claim 1, wherein said mixtures are introduced separately to at least one further condensing environment providing a further condensing medium in order to separately condensate said further condensing medium onto the aerosol particles of the mixtures and to further grow said aerosol particles before detecting.

4. The method according to claim 1, wherein said first condensing medium comprises low vapour pressure and high surface tension compared to further condensing mediums, and wherein each of said further condensing mediums comprise high vapour pressure and high diffusivity compared to the first condensing medium.

5. The method according to claim 1, wherein the flow rate of the aerosol gas stream is kept essentially constant and higher in relation to the saturated particle-free carrier flow, said flow rate of the aerosol gas stream in the range of 2-5 l/min, and wherein the saturated particle-free carrier flow rate is varied, said saturated particle-free carrier flow in the range of 0.05 and 5 l/min.

6. The method according to claim 1, wherein said aerosol particle stream comprises lower temperature than the saturated particle-free carrier flow before mixing, and wherein the first condensing environment comprises lower temperature than the mixture before entering into said first condensing environment, and wherein the method further comprises the step of further growing the aerosol particles in a further condensing environment before detecting, the further condensing environment comprises
higher temperature than the first condensing environment, if a further condensing medium used in said further condensing environment comprises higher diffusivity in air than heat; and
lower temperature than a first saturating environment comprising said further condensing medium, if the further condensing medium used in said further condensing environment comprises lower diffusivity in air than heat.

7. The method according to claim 1, wherein the original lowest particle size varies between 1-5 nm before growing by condensation and wherein said particles are grown to optically detectable size.

8. The method according to claim 1, wherein said mixing is turbulent and/or adiabatic.

9. An arrangement for detecting different size or size distribution of aerosol particles of an aerosol gas stream, the arrangement comprising:
a saturating environment adapted to saturate particle-free carrier flow by a first condensing medium and to provide saturated particle-free carrier flow, wherein said saturating environment is provided within a saturator, said saturator comprising sintered tubing surrounded by said first condensing medium inside a casing, and wherein a porosity of said sintered tubing is chosen so that a surface tension of said first condensing medium prevents it to flow through the pores as a liquid;

a mixing section comprising anti-static plastic for mixing said saturated particle-free carrier flow with said aerosol gas stream comprising said aerosol particles;

wherein the arrangement comprises a controllable valve and/or adjustable pump and is adapted for providing at least two separate mixtures of said saturated particle-free carrier flow and aerosol particles, said mixtures having different saturation ratios by changing the flow rate of the saturated particle-free carrier flow and/or the aerosol gas stream sequentially by said controllable valve and/or adjustable pump;

wherein the arrangement is adapted for introducing said mixtures separately to a first condensing environment by changing the flow rate of the saturated particle free flow and/or the aerosol gas stream sequentially by said controllable valve and/or adjustable pump, said first condensing environment being adapted to condense said first condensing medium onto the aerosol particles of the mixtures so that the mixture having the first saturation ratio is adapted to condense onto the particles having different initial size than the mixture having the second different saturation ratio, wherein said condensation causes the aerosol particles to grow; and wherein the arrangement comprises a particle counter for detecting said growth of aerosol particles of different mixtures separately after said condensation.

10. The arrangement according to claim 9, wherein the arrangement is adapted to provide different saturation ratios by changing the flow rate of the saturated particle- free carrier flow and/or the aerosol gas stream, and/or by altering the temperature difference between the saturated particle-free carrier flow and the aerosol gas stream.

11. The arrangement according to claim 9, wherein the arrangement comprises at least one further condensing environment with a further condensing medium, and the arrangement is adapted to introduce said mixtures separately to said at least one further condensing environment in order to separately condensate said further condensing medium on the aerosol particles of the mixtures and to further grow said aerosol particles before detecting.

12. The arrangement according to claim 9, wherein the arrangement is adapted to keep the flow rate of the aerosol gas stream essentially constant and higher in relation to the saturated particle-free carrier flow, said flow rate of the aerosol gas stream in the range of 2-5 l/min, and wherein the arrangement is adapted to vary saturated particle-free carrier flow rate between 0.05 and 5 l/min wherein the flow rate of the aerosol gas stream is kept essentially constant and higher in relation to the saturated particle-free carrier flow, said flow rate of the aerosol gas stream in the range of 2-5 l/min, and wherein the saturated particle-free carrier flow rate is varied, said saturated particle-free carrier flow in the range between 0.05 and 5 l/min.

13. The arrangement according to claim 9, the arrangement further comprising a further condensing environment to grow said aerosol particles prior to said detection, wherein the arrangement comprises a temperature controller to adjust the temperature of the aerosol particle stream lower than the temperature of the saturated particle-free carrier flow before mixing, the temperature of the first condensing environment lower than the temperature of the mixture before entering into the first condensing environment, and the temperature of the further condensing environment higher than the temperature of the first condensing environment, if a further condensing medium used in said further condensing environment comprises higher diffusivity in air than heat; and lower than the temperature of the saturating environment comprising said further condensing medium, if the further condensing medium used in said further condensing environment comprises lower diffusivity in air than heat.

14. The arrangement according to claim 9, wherein the arrangement is adapted to determine the original lowest particle size of the particle detected by monitoring the used saturation ratio, when the correlation of the saturation ratio and the lowest size of the particle to be activated and growth by said saturation ratio is known.

15. The arrangement according to claim 9, wherein the arrangement is adapted to determine the used saturation ratio by monitoring flow rate of at least one of the following: saturated particle-free carrier flow, and flow comprising aerosol particles to be detected.

16. The arrangement according to claim 9, wherein the first condensing environment comprises condensing chamber having growth section of a conical tubing the inner diameter of which expands along the direction of the flow inside said tubing.

17. The arrangement according to claim 9, wherein the saturating environment is provided within a saturator, and wherein the arrangement is adapted to control the flow rates through the saturator and/or the excess flow by said controllable valve and/or adjustable pump.

18. The arrangement according to claim 9, the arrangement further comprising a second condensation environment to grow said aerosol particles prior to said detection, said second condensation environment comprising a tube heated and wetted by a second condensing medium.

19. A device for detecting different size or size distribution of aerosol particles of an aerosol gas stream, the device comprising:

a saturating environment adapted to saturate particle-free carrier flow by a first condensing medium and to provide saturated particle-free carrier flow;

a mixing section comprising anti-static plastic for mixing said saturated particle-free carrier flow with said aerosol gas stream comprising said aerosol particles;

wherein the device comprises a controllable valve and/or adjustable pump and is adapted for providing at least two separate mixtures of said saturated particle-free carrier flow and aerosol particles, said mixtures having different saturation ratios by changing the flow rate of the saturated particle-free carrier flow and/or the aerosol gas stream sequentially by said controllable valve and/or adjustable pump;

wherein the device is adapted for introducing said mixtures separately to a first condensing environment by changing the flow rate of the saturated particle-free carrier flow and/or the aerosol gas stream sequentially by said controllable valve and/or adjustable pump., said first condensing environment being adapted to condense said first condensing medium onto the aerosol particles of the mixtures so that the mixture having the first saturation ratio is adapted to condense onto the particles having different initial size than the mixture having the second different saturation ratio, wherein said condensation causes the aerosol particles to grow; and wherein the device comprises a particle counter for detecting said growth of aerosol particles of different mixtures separately after said condensation; and wherein the device is adapted to determine original lowest particle size of the particle detected by monitoring the used saturation ratio so that the higher the saturation ratio the smaller the lowest original particle size.

* * * * *